United States Patent
Royse et al.

(10) Patent No.: US 7,666,136 B2
(45) Date of Patent: Feb. 23, 2010

(54) RETRACTOR

(75) Inventors: Alistair Royse, Eltham (AU); David Berry, North Ringwood (AU); Brett Hamilton, Tooradin (AU); Michael Kerr, Ivanhoe (AU)

(73) Assignee: Research Surgical Pty Ltd, Greensborough, Victoria (AU)

( * ) Notice: Subject to any disclaimer, the term of this patent is extended or adjusted under 35 U.S.C. 154(b) by 599 days.

(21) Appl. No.: 10/511,967

(22) PCT Filed: Apr. 22, 2003

(86) PCT No.: PCT/AU03/00478

§ 371 (c)(1),
(2), (4) Date: Apr. 12, 2005

(87) PCT Pub. No.: WO03/090626

PCT Pub. Date: Nov. 6, 2003

(65) Prior Publication Data

US 2005/0177028 A1    Aug. 11, 2005

(30) Foreign Application Priority Data

Apr. 26, 2002    (AU) .................................... PS1985

(51) Int. Cl.
*A61B 1/32*    (2006.01)
(52) U.S. Cl. ................ 600/234; 600/227; 600/231
(58) Field of Classification Search ............. 600/226, 600/227, 231–234
See application file for complete search history.

(56) References Cited

U.S. PATENT DOCUMENTS

| | | | | |
|---|---|---|---|---|
| 3,070,088 | A | * | 12/1962 | Brahos ........................ 600/234 |
| 3,227,156 | A | * | 1/1966 | Gauthier ...................... 600/231 |
| 4,155,355 | A | * | 5/1979 | Yamamoto ................... 600/233 |
| 4,813,401 | A | | 3/1989 | Grieshaber |
| 4,829,985 | A | * | 5/1989 | Couetil ........................ 600/232 |
| 4,896,661 | A | * | 1/1990 | Bogert et al. ............. 606/86 R |
| 4,949,707 | A | * | 8/1990 | LeVahn et al. .............. 600/234 |
| 5,000,163 | A | * | 3/1991 | Ray et al. ..................... 600/233 |
| 5,297,538 | A | * | 3/1994 | Daniel .......................... 600/206 |
| 5,529,571 | A | * | 6/1996 | Daniel .......................... 600/219 |
| 6,431,025 | B1 | * | 8/2002 | Koros et al. ............... 74/577 M |
| 6,796,986 | B2 | * | 9/2004 | Duffner ......................... 606/87 |
| 7,276,024 | B1 | * | 10/2007 | Royse et al. ................. 600/210 |
| 2002/0177753 | A1 | * | 11/2002 | Dobrovolny ................ 600/234 |

FOREIGN PATENT DOCUMENTS

| | | |
|---|---|---|
| EP | 803228 | 10/1997 |
| WO | WO 01/06934 | 2/2001 |

OTHER PUBLICATIONS

International Search Report.
International Preliminary Examination Report.

* cited by examiner

*Primary Examiner*—Cris L Rodriguez
*Assistant Examiner*—Hao D Mai
(74) *Attorney, Agent, or Firm*—Harness, Dickey & Pierce, P.L.C.

(57) ABSTRACT

A retractor for use in surgery, has arms (2, 4) pivotal into a V-shaped configuration. Blades (16) are carried by the arms via mounting portions (16*a*) which can slide along the arms to provide adjustment in position with the blades being locked in that position simply by skewing the mounting portions on the arms.

19 Claims, 6 Drawing Sheets

RETRACTOR

CROSS-REFERENCE TO RELATED APPLICATIONS

This application is a National Stage of International Application No. PCT/AU03/00478, filed Apr. 22, 2003, which claims the benefit of Australian Application No. P51985/02, filed on Apr. 26, 3003. The disclosures of the above applications are incorporated herein by reference.

This invention relates to retractors for use in surgery, and more particularly but not exclusively, to retractors for use in chest surgery.

The retractor in accordance with the present invention is a modified version of the surgical retractor disclosed in our International patent application PCT/AU00/00887 the full disclosure of which is hereby incorporated by reference. In summary, the retractor disclosed in our earlier International patent application as aforesaid comprises two arms each adapted to carry a retractor blade engageable with one side of an incision, the two arms being connected at one end portion by a pivot such that the arms can be pivoted between a closed position and an adjustable open position in which the arms define a substantially V-shaped configuration in which the blades maintain the blades of the incision in inclined relation. The arms are retained in an open position by a curved bar carried by one of the arms at an end portion thereof remote from the pivot, the curved bar being in the form of a toothed rack engageable with a driving pinion carried by the other arm so that rotation of the driving pinion will cause opening movement of the arms. The modification to which this present invention relates concerns the design of the arm-s and the associated mounting for the blades and which results in a somewhat simplified construction.

According to the invention, there is provided a retractor for use in surgery having two arms each removably mounting a blade, the arms being connected by a pivot at one end portion so that the arms can be swung between a closed position and an adjustable open position in which the arms define a substantially V-shaped configuration in which the blades maintain the sides of an incision in inclined relation in the open position, each blade having a mounting portion engageable on the arm so as to at least partially surround the arm for displacement longitudinally along the arm into a selected position, the blade being lockable to the arm against longitudinal displacement out of its selected position in at least one direction by displacement between the mounting portion and the arm after movement into the selected position.

Further according to the present invention there is provided a retractor for use in surgery, the retractor having two arms each adapted to carry a blade engageable with one side of an incision, the two arms being connected by a pivot at one end portion such that the arms can be pivoted between a closed position and an adjustable open position in which the arms define a substantially V-shaped configuration in which the blades maintain the sides of the incision in inclined relation, and means for retaining the arms in the open position, wherein each retractor blade has a mounting portion engageable on the arm so as to at least partially surround the arm and displaceable longitudinally along the arm, and wherein the arm is shaped to provide a series of abutment edges spaced in the longitudinal direction of the arm and engageable with a part of the mounting portion of the blade so as to lock the mounting portion to the arm against displacement from a selected position along the arm at least in one longitudinal direction.

Still further according to the invention there is provided a retractor for use in surgery, the retractor having two arms each adapted to carry a blade engageable with one side of an incision, the two arms being connected by a pivot at one end portion such that the arms can be pivoted between a closed position and an adjustable open position in which the arms define a substantially V-shaped configuration in which the blades maintain the sides of the incision in inclined relation, and means for retaining the arms in the open position, wherein each retractor blade has a mounting portion engageable on the arm so as to at least partially surround the arm and displaceable longitudinally along the arm, and wherein the arm is shaped to provide a series of abutment edges spaced in the longitudinal direction of the arm and engageable with a part of the mounting portion of the blade when the mounting portion is inclined relative to the arm after movement along the arm into a selected position so as to lock the mounting portion to the arm against displacement from the selected position at least in one longitudinal direction.

The abutment edges may be formed by series of grooves or notches spaced along the arm.

In one form, the exterior shape of the arm and the interior shape of the mounting portion are so related that the mounting portion and associated retractor blade is able to freely rotate about the axis of the arm. In an alternative form, the exterior shape of the arm and the interior shape of the mounting portion are so related that the mounting portion and associated retractor blade is able to be locked to the arm in a selected angular position against rotation about the axis of the arm.

In one particularly preferred embodiment of the invention, the arm is of polygonal cross-section, for example hexagonal cross-section. The mounting portion for a retractor blade required to rotate about the axis of the arm has smooth interior surface of part-cylindrical form able to rotate about the arm. The mounting portion of a retractor blade required to be locked against rotation relative to the arm has a part-cylindrical inner surface having longitudinal grooves adapted to engage with corner portions of the polygonal cross-section in order to lock the mounting portion against rotation in a selected angular position relative to the arm. In both cases, the diameter of the inner surface of the mounting portion is slightly greater than the diameter of the polygonal cross-section to permit the axis of the mounting portion to incline or skew through a small angle relative to the axis of the arm to thereby permit locking of the mounting portion in a selected position along the length of the arm by co-operation with an adjacent abutment edge.

The arm may alternatively be of circular cross-section having a series of longitudinally directed notched ridges or grooves to co-operate with the inner surface of the mounting portion.

Advantageously, the mounting portion and associated retractor blade are formed integrally as a single component.

Although the blade mounting system of the invention has particular advantage when incorporated in a retractor as disclosed in our earlier International patent application specified previously, it also can be incorporated with advantage into other forms of surgical retractor.

Accordingly, a further aspect of the invention provides a retractor for use in surgery having two arms each removably mounting a blade, each blade having a mounting portion engageable on the arm so as to at least partially surround the arm for displacement longitudinally along the arm into a selected position, the blade being lockable to the arm against longitudinal displacement out of its selected position in at least one direction by displacement between the mounting portion and the arm after movement into the selected position.

An embodiment of the invention will now be described by way of example only with reference to the accompanying drawings in which:—

Figure 1:
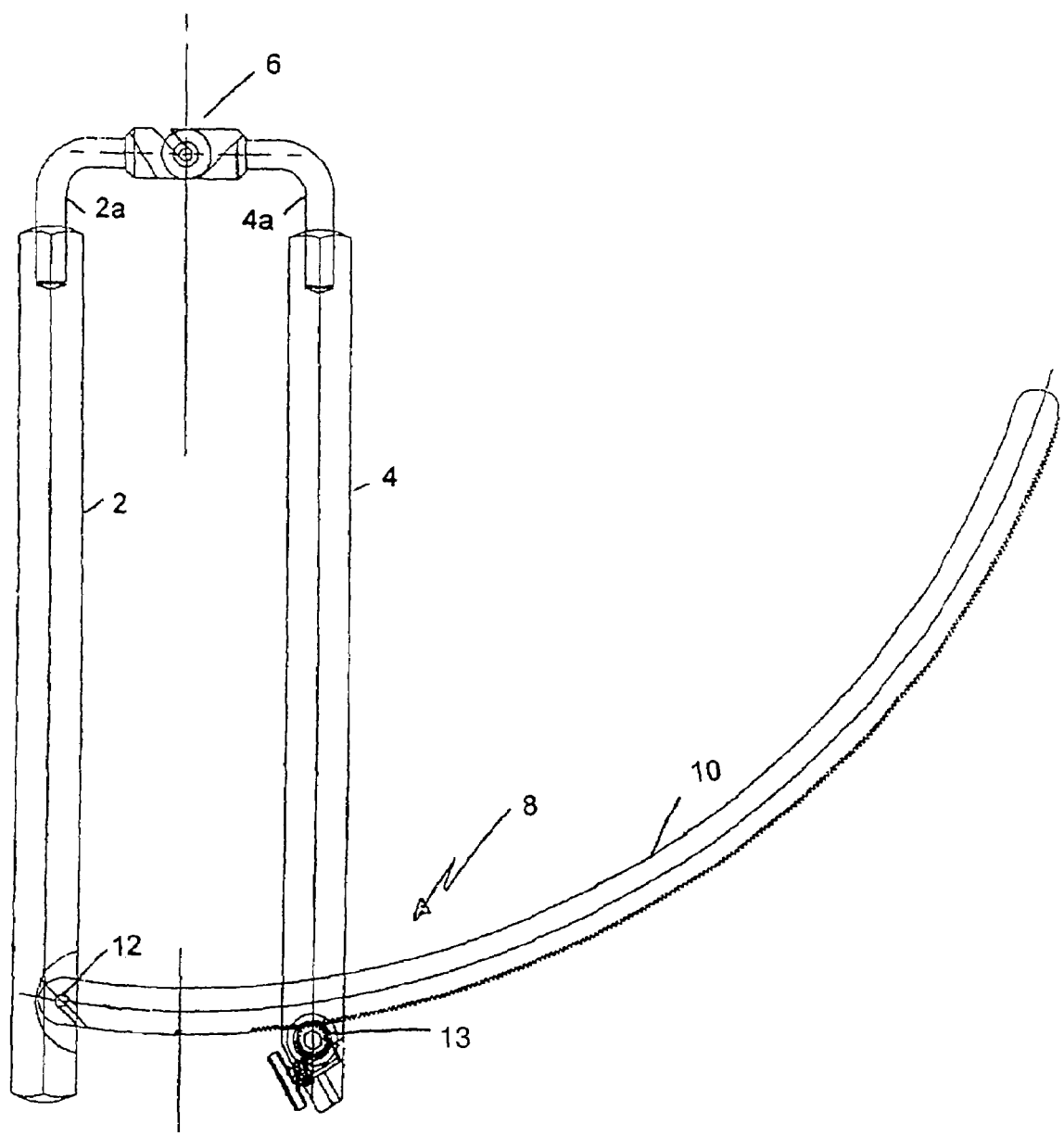
FIG. 1 is a side view showing a retractor in accordance with the preferred embodiment of the invention.

The retractor in accordance with the preferred embodiment of the invention is of the same basic construction as the retractor of the preferred embodiment of the invention disclosed in our International patent application PCT/AU00/00887. Briefly, the retractor shown in FIG. 1, is principally for use in chest surgery and comprises two arms 2, 4 which are connected by a pivot 6 at their upper ends such that the arms 2, 4 can be pivoted between a closed position in which the arms are substantially parallel and an open position in which the arms 2, 4 are inclined to define a substantially V-shaped configuration. The arms 2, 4 each carry at least one blade (not shown in FIG. 1) for contact with tissue of the patient on either side of an incision such that opening of the arms 2, 4 opens the incision in a V-shape. The blades are replaceable and are available in a range of sizes to provide for various sizes and/or obesities of patients. The two arms 2, 4 are provided with locking means 8 to releasably hold the arms 2, 4 in a variable open position.

In the preferred embodiment, the locking means 8 includes an arm in the form of a curved rack 10, one end of which is fixed to an end of the arm 2 by a pivot 12. A toothed outer edge of the rack 10 engages a driving pinion 13, rotatably mounted at the end of the other arm 4. The pinion 13 is associated with a ratchet and pawl mechanism having a first "ratchet" state in which rotation of the pinion 13 in only one direction is allowed such that only opening movement of the arms 2, 4 is possible. A second "free" state allows both opening and closing movement of the arms 2, 4. The state of the mechanism can be changed by switching of a pawl release. The pinion 13 is drivable by means of a crank handle in order to open the arms 2, 4 and hence to open the incision. The crank handle is detachable from the pinion to reduce interference during surgery. Reference should be made to our earlier International patent application for full details of the pivot and also of a rack and pinion drive assembly.

In contrast to the arms of the retractor shown in our earlier International patent application as aforesaid, the arms 2, 4 in accordance with the preferred embodiment of the invention are principally of solid one-piece construction of hexagonal cross-section save for reduced diameter connecting portions 2a, 4a at the end associated with the pivot 6. As shown in FIGS. 2 to 5, each arm 2, 4 is formed along its length with a series of notches or grooves 14 evenly spaced along the length of the arm and positioned to intersect at least some, and as shown all, of the corner portions of the hexagonal cross-section. Attachment of a retractor blade 16 to the arm 2 or 4 is effected by means of a part-cylindrical mounting portion 16a able to be slid onto the reduced diameter portion of the arm adjacent the pivot and then to be displaced longitudinally along the substantive hexagonal part of the arm. The mounting portion 16a has a circumferential extent in excess of 180° to ensure that when it has been mounted on the arm by sliding over the end of the hexagonal part it cannot accidentally dislodged from the arm. When it is desired that the associated retractor blade is to be locked in a predetermined angular position about the axis of the arm such as when the blade is to be used to effect a horizontal displacement, the interior surface of the mounting portion 16a is formed with a series of relatively closely spaced longitudinal grooves 16b of V-shaped section. The cross-sectional shape of these grooves corresponds substantially to the cross-section of each of the corner portions of the hexagonal arm so that when the mounting portion 16a has been moved into a predetermined angular position on the reduced diameter portion and then slid longitudinally onto the hexagonal part, certain of the grooves 16b on the interior surface of the mounting portion 16a will interlock with the adjacent corner portions of the hexagonal arm to thereby lock the mounting portion 16a and hence the associated retractor blade 16 against rotation relative to the arm. The grooves 16b on the interior surface of the mounting portion 16a are spaced by a relatively small pitch distance whereby to permit relatively fine adjustment of the angular position in which the mounting portion is to be retained.

When the retractor blade 16 is to be used in situations where it needs to be able to freely rotate about the axis of the arm, such as for use on one side of an incision during internal mammary artery harvest with vertical displacement, the interior surface of the mounting portion 16a is smooth rather grooved whereby the mounting portion is able to rotate about the axis of the arm.

Figure 4:
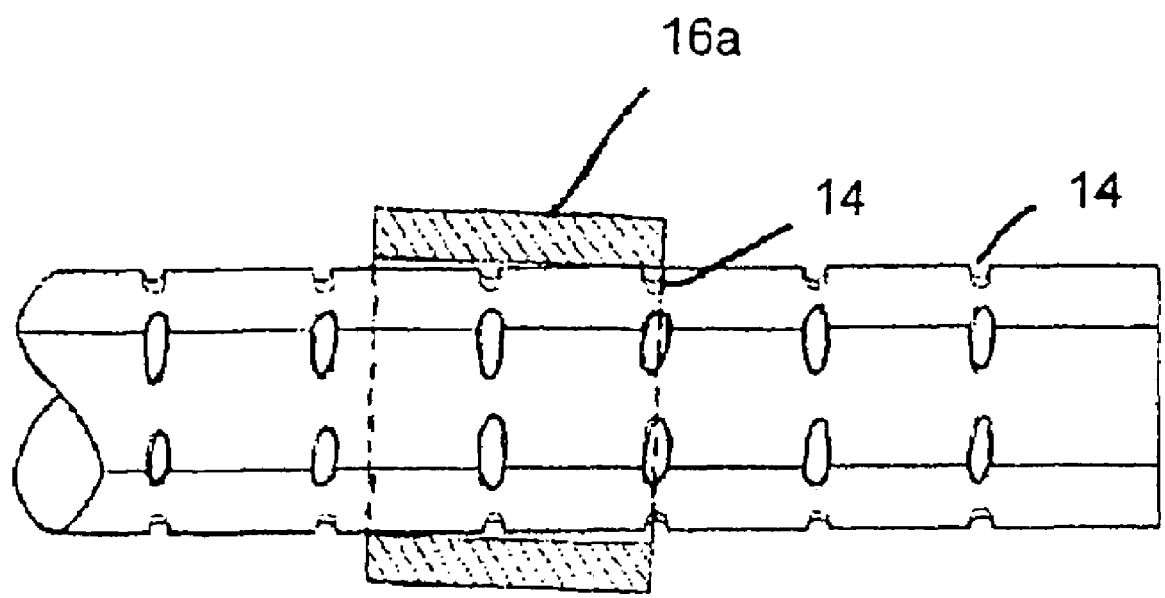
FIGS. 4 and 5 show schematically the manner in which the mounting portion of the retractor blade interacts with the arm to secure the mounting portion in a selected position along the length of the arm.
Figure 5:
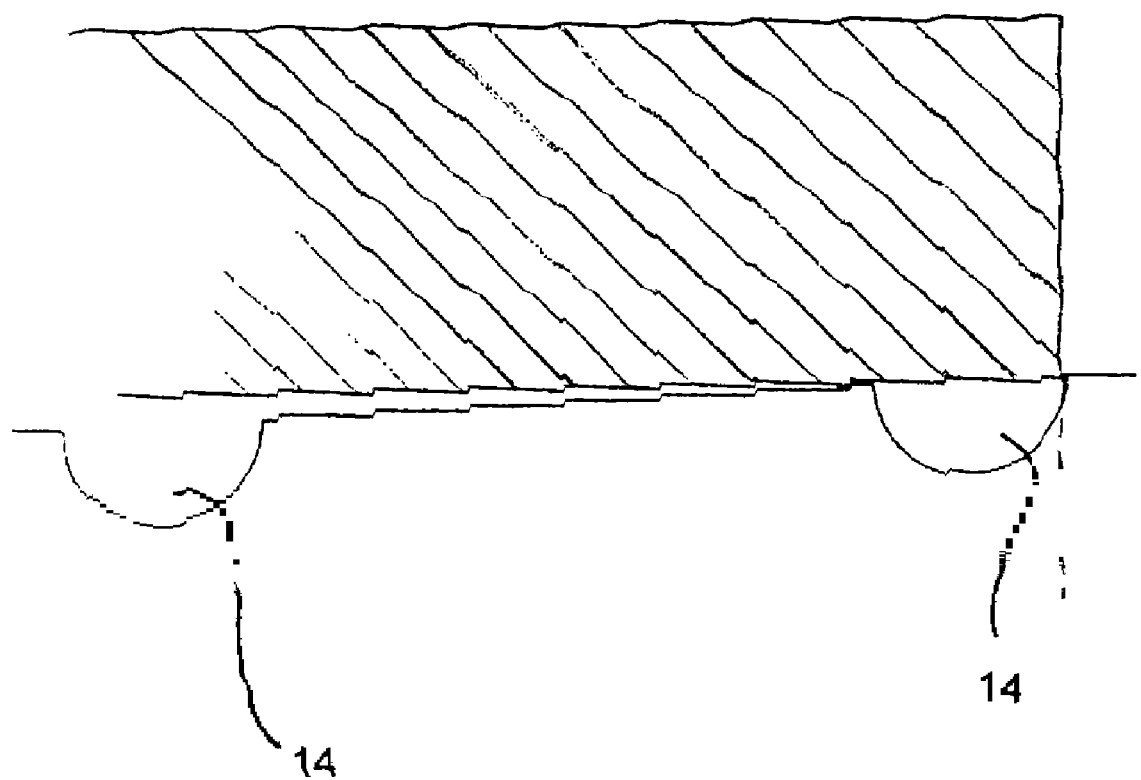

In either case (rotatably lockable and freely rotatable), the internal diameter of the mounting portion 16a is slightly larger than the diameter of the hexagonal part of the arm and as a result the mounting portion is able to skew or tilt so that its axis is inclined by a small angle relative to the axis of the arm (see FIGS. 4 and 5). This inclination in conjunction with the notches 14 formed along the length of the hexagonal corner portions of the arm is used to provide securement of the mounting portion 16a in one of a multiplicity of predetermined positions along the length of the arm as will be understood with reference to FIGS. 4 and 5 from which it will be seen that the slight inclination of the mounting portion 16a will cause the inner edge of the mounting portion to engage with the adjacent one of the notches 14 which thereby forms an abutment edge to prevent further longitudinal displacement. Although it will be understood that the engagement of the inner edge of the mounting portion with the adjacent notch only occurs at one end of the mounting portion (as shown at the right hand end) and will thereby prevent further displacement to the right, the opposite end of the mounting portion will be similarly skewed and movement of the mounting portion in the opposite direction will be stopped as soon as the left hand end engages the next adjacent notch. It will be understood that with this mounting and locking mechanism, the mounting portion is able to be locked in any one of a number of incrementally spaced positions along the arm, determined by the pitch spacing of the notches. Movement of the mounting portion along the arm can be accomplished by holding the mounting portion so that it is in parallel, non-skewed, relationship with the arm and can thereby be easily slid along the arm until the selected position is reached.

Particularly advantageously, the retractor blade 16 and its mounting portion 16a are integrally formed as a one-piece construction. This not only simplifies manufacture but also significantly assists cleaning and sterilisation.

Figure 2:
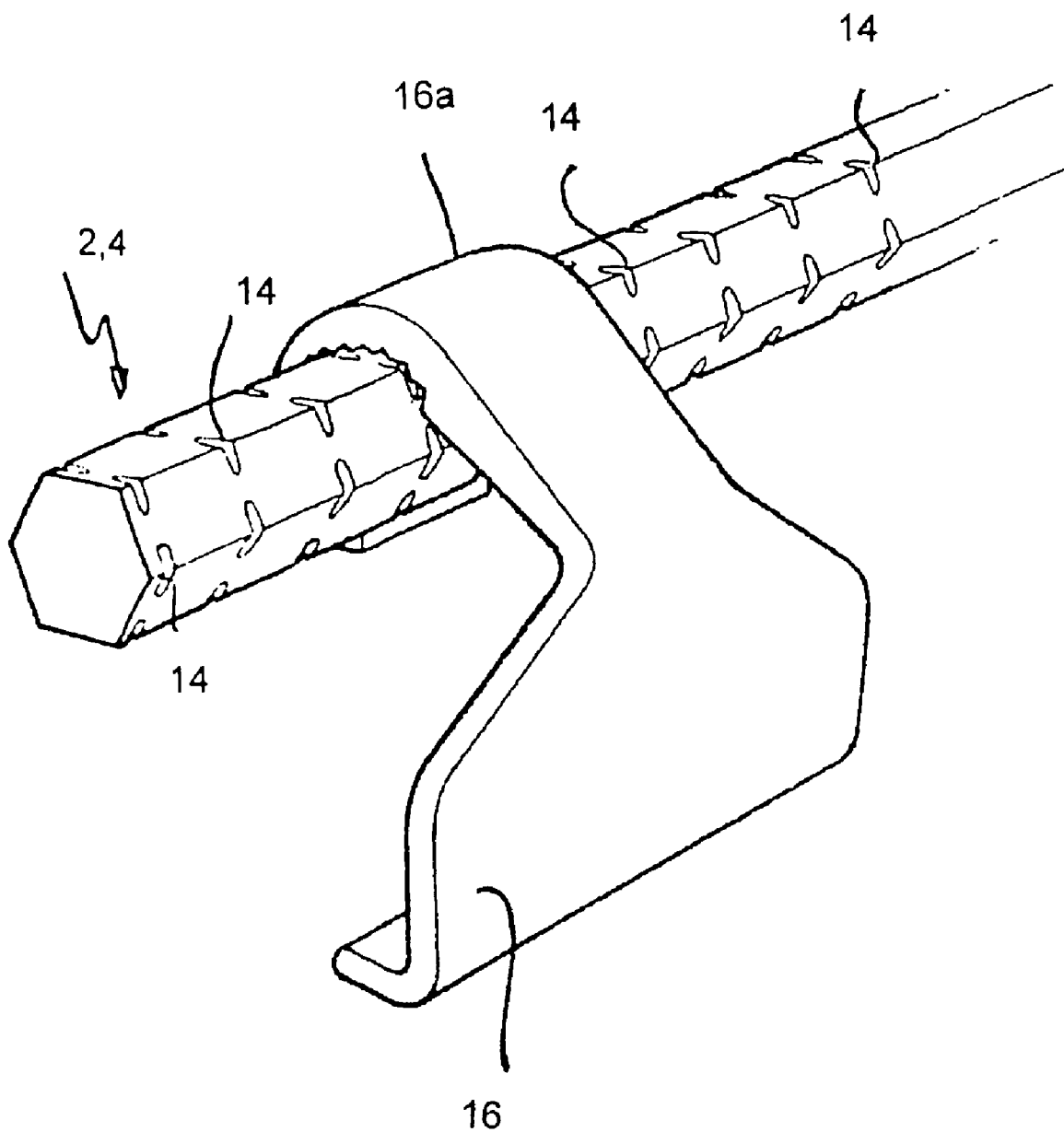
FIG. 2 is a fragmentary enlarged perspective view showing part of an arm of the retractor carrying a retractor blade and associated mounting portion.
Figure 3:
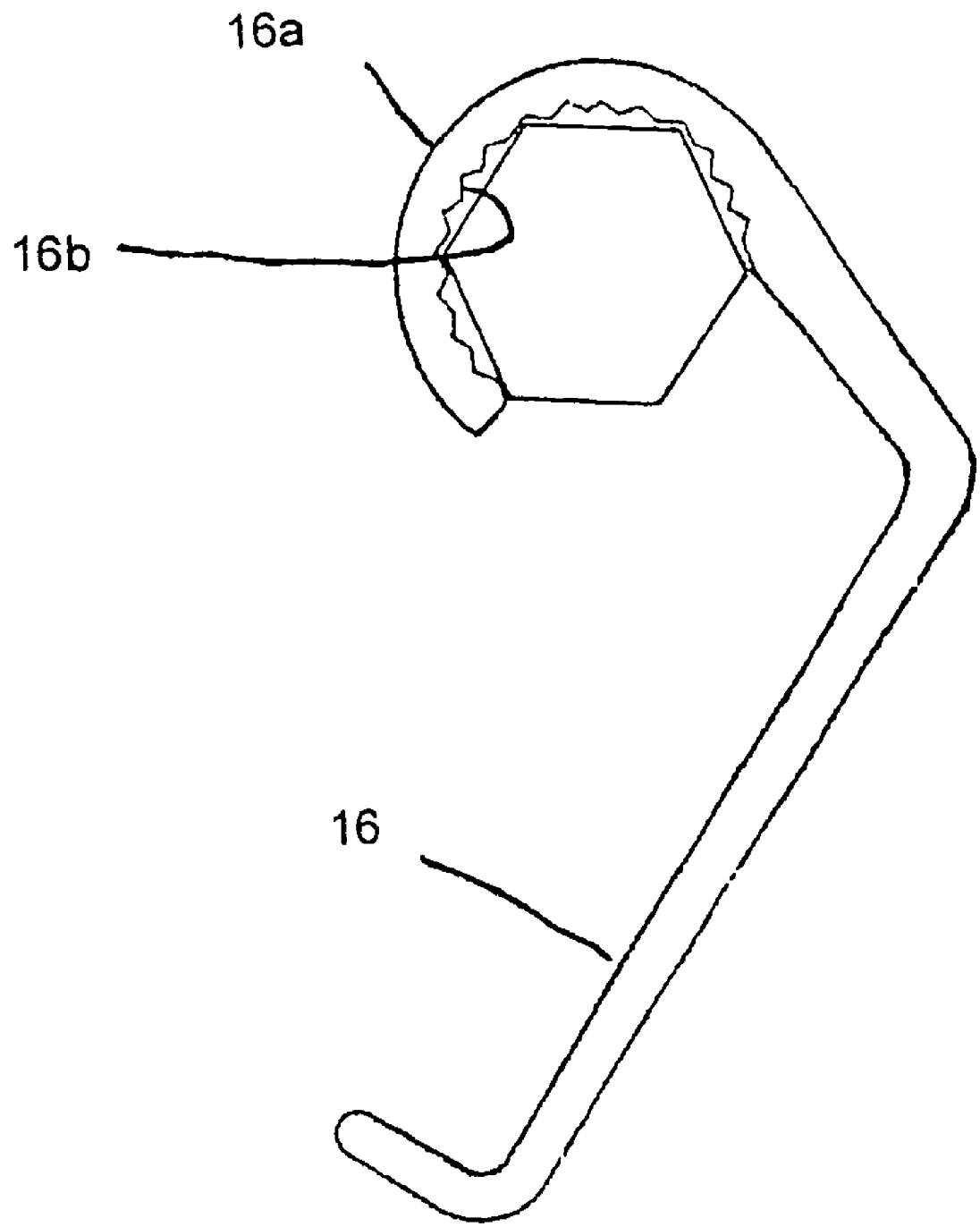
FIG. 3 is an end view equivalent to FIG. 2.
Figure 6:
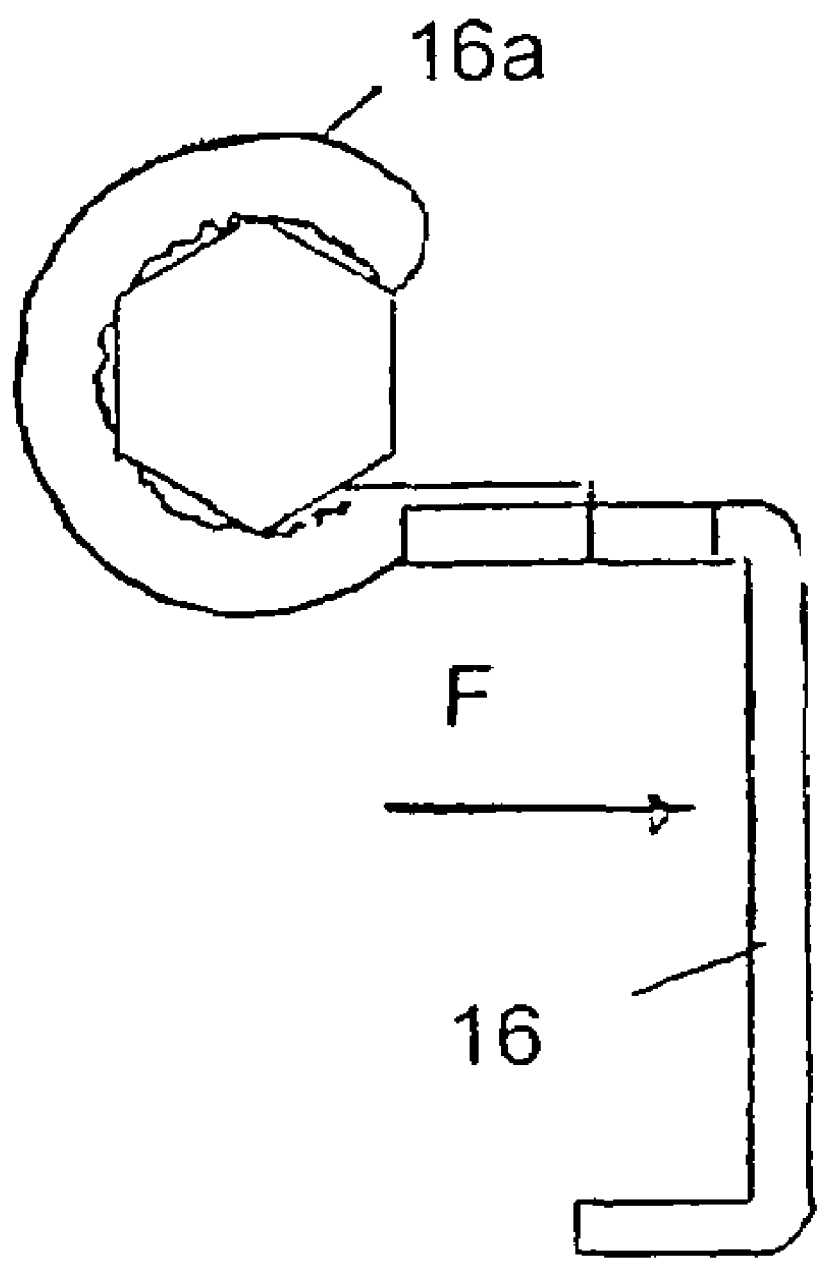
FIG. 6 is an end view similar to FIG. 3 but showing a modified, and preferred, configuration of the blade mounting portion.

FIG. 6 shows a retractor blade 16 in which its mounting portion 16a is orientated oppositely to that shown in FIGS. 2 and 3 so that the reactive force acting on the blade during use as indicated by the arrow F in FIG. 6 tends to cause the part-cylindrical mounting portion 16a to "close" into tighter engagement with the arm. This is preferred over the configuration shown in FIGS. 2 and 3 in which the reactive force acting on the blade during use will act in a sense to "open" the part-cylindrical mounting portion and which might lead to a reduction in the locking effect between the mounting portion and arm depending on the rigidity of the mounting portion.

The adjustable mounting system provided by the co-operation of the mounting portion and the hexagonal shape of the arm represents-itself a significant simplification of the structure both of the arm and the mounting portion. This simplification likewise facilitates reduced manufacturing costs and also the arm itself represents a component which is relatively easy to clean and sterilise.

The embodiment has been described by way of example only and modifications are possible within the scope of the invention. For example, although as described the main parts of the arms are of hexagonal cross-section, other polygonal cross-sections providing a series of angularly spaced corner portions could be used. In principle, it would even be possible for the arms to be generally of circular cross-section with longitudinal ribs or grooves to co-operate with the grooves on the internal surface of the mounting portion and series of transverse notches possibly defined by annular grooves to co-operate with the edge of the mounting portion when skewed in order to lock the mounting portion in a selected longitudinal position as previously described. Although as described, the mounting portion of the retractor blade only partially surrounds the arm, constructions in which the mounting portion has a circumferential extent of 360° would be feasible although not especially preferred.

Although the blade mounting system provided by the co-operation between the arms and blade mounting portions has been described in relation to a retractor in which the arms are pivotal between a closed position and an adjustable open position in which they define a substantially V-shaped configuration, in its broader senses the invention is applicable to other forms of retractor having a different form of mounting and movement of the opposed arms.

The invention claimed is:

1. A surgical retractor comprising:
two arms, each arm comprising a generally polygonal cross-section and an outer surface including a plurality of sides and a plurality of notches, each notch located at a discrete position around the perimeter of the arm and between a first end of the arm and a second end of the arm and formed at an intersection of two adjacent sides of the outer surface;
each arm being pivotally connected to the other arm at the first end such that the arms can be pivoted between a closed position in which the arms are substantially parallel to one another and an open position in which the arms have a substantially V-shaped configuration;
a lock for retaining the arms in the open position;
a plurality of retractor blades, at least one retractor blade carried by each arm, each blade comprising a mounting portion cooperable with the arm for locating the retractor blade at any of the plurality of locations around the perimeter of the arm and between the first end and the second end of the arm, the mounting portion comprising an inner surface extending around more than half of the perimeter of the arm;
wherein when the retractor blade is in an unlocked position the inner surface is substantially parallel to the surface of the arm and the retractor blade is moveable between the first end and second end of the arm; and
wherein in a locked position the inner surface is askew to the surface of the arm and at least one edge of the mounting portion is engaged with at least one notch and the retractor blade is not movable between the first end and second end of the arm.

2. A retractor according to claim 1, wherein at least some of the notches are transverse to the intersection of two adjacent sides of the outer surface.

3. A retractor according to claim 2, wherein the inner surface of the mounting portion comprises a plurality of longitudinal grooves distributed around the inner surface that are cooperable with the plurality of notches to enable the mounting portion to be retained on the arm in a selected one of a plurality of positions around the perimeter of the arm when in the locked position.

4. A retractor according to claim 1 wherein the mounting portions of some of the plurality of retractor blades freely rotate about the longitudinal axis of the arm and the mounting portions of others of the plurality of retractor blades are configured to enable the mounting portion to be retained on the arm in a selected one of a plurality of angular positions relative to the longitudinal axis of the arm.

5. A retractor according to claim 4, wherein the arm comprises a polygonal cross-section having at least five sides.

6. A retractor according to claim 5, wherein at least some of the notches are transverse to at least some of the edges formed at the intersections of the sides of the arm.

7. A retractor according to claim 4, wherein the arm comprises a hexagonal cross-section.

8. A retractor according to claim 7, wherein at least some of the notches are transverse to at least some of the edges of the hexagonal cross-section.

9. A retractor according to claim 4, wherein each blade with its mounting portion is of one-piece construction.

10. A surgical retractor comprising:
two arms, each arm extending from a first end to a second end along a first longitudinal axis and being pivotally connected to the other arm at the first end such that the arms can be pivoted between a closed position in which the arms are substantially parallel to one another and an open position in which the arms have a substantially V-shaped configuration;
a lock for retaining the arms in the open position;
each arm further comprising an outer surface comprising six faces and a plurality of edges, each edge formed at an intersection of two adjacent faces;
the outer surface further comprising a plurality of discrete notches, each notch being formed transversely across one of the plurality of edges of the outer surface;
a plurality of retractor blades, at least one retractor blade carried by each arm, each blade comprising a mounting portion extending along a second longitudinal axis from a first edge to a second edge and being cooperable with the arm for locating the retractor blade at any of a plurality of locations on the outer surface of the arm, the mounting portion comprising an inner surface extending around at least three faces of the outer surface of the arm;
wherein when the retractor blade is in an unlocked position the second longitudinal axis is substantially parallel to the first longitudinal axis and the retractor blade is moveable between the first end and second end of the arm; and
wherein in a locked position the second longitudinal axis is not substantially parallel to the first longitudinal axis and at least one edge of the mounting portion is engaged with at least one notch and the retractor blade is not movable between the first end and second end of the arm.

11. A retractor according to claim 10 wherein the mounting portions of some of the plurality of retractor blades freely rotate about the longitudinal axis of the arm and the mounting portions of others of the plurality of retractor blades are configured to enable the mounting portion to be retained on the arm in a selected one of a plurality of angular positions relative to the longitudinal axis of the arm.

12. A retractor according to claim 10, wherein the inner surface of the mounting portion comprises a plurality of longitudinal grooves distributed around the inner surface that are cooperable with the plurality of notches to enable the mounting portion to be retained on the arm in a selected one of a plurality of positions on the outer surface of the arm when in the locked position.

13. A retractor according to claim 10, wherein the arm comprises a hexagonal cross-section.

14. A retractor according to claim 10, wherein each blade with its mounting portion is of one-piece construction.

15. A surgical retractor comprising:
two arms, each arm extending from a first end to a second end along a first longitudinal axis and being pivotally connected to the other arm at the first end such that the arms can be pivoted between a closed position in which the arms are substantially parallel to one another and an open position in which the arms have a substantially V-shaped configuration;
a lock for retaining the arms in the open position;
each arm further comprising an outer surface comprising at least five faces and at least five edges and a plurality of discrete notches, each notch being formed transversely across one of the plurality of edges of the outer surface such that at least two of the plurality of notches are formed in at least one of the plurality of edges;
a plurality of retractor blades, at least one retractor blade carried by each arm, each blade comprising a mounting portion extending along a second longitudinal axis from a first edge to a second edge and being cooperable with the arm for locating the retractor blade at any of a plurality of locations on the outer surface of the arm, the mounting portion comprising an inner surface extending around at least three faces of the outer surface of the arm;
wherein when the retractor blade is in an unlocked position the second longitudinal axis is substantially parallel to the first longitudinal axis and the retractor blade is moveable between the first end and second end of the arm; and
wherein in a locked position the second longitudinal axis is not substantially parallel to the first longitudinal axis and at least one edge of the mounting portion is engaged with at least one notch and the retractor blade is not movable between the first end and second end of the arm.

16. A retractor according to claim 15 wherein the mounting portions of some of the plurality of retractor blades freely rotate about the longitudinal axis of the arm and the mounting portions of others of the plurality of retractor blades are configured to enable the mounting portion to be retained on the arm in a selected one of a plurality of angular positions relative to the longitudinal axis of the arm.

17. A retractor according to claim 15, wherein the inner surface of the mounting portion comprises a plurality of longitudinal grooves distributed around the inner surface that are cooperable with the plurality of notches to enable the mounting portion to be retained on the arm in a selected one of a plurality of positions on the outer surface of the arm when in the locked position.

18. A retractor according to claim 15, wherein the arm comprises a hexagonal cross-section.

19. A retractor according to claim 15, wherein each blade with its mounting portion is of one-piece construction.

\* \* \* \* \*

UNITED STATES PATENT AND TRADEMARK OFFICE
CERTIFICATE OF CORRECTION

PATENT NO. : 7,666,136 B2
APPLICATION NO. : 10/511967
DATED : February 23, 2010
INVENTOR(S) : Royse et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1099 days.

Signed and Sealed this

Twenty-eighth Day of December, 2010

David J. Kappos
*Director of the United States Patent and Trademark Office*